US009668830B2

(12) United States Patent
Lu

(10) Patent No.: US 9,668,830 B2
(45) Date of Patent: Jun. 6, 2017

(54) WISDOM TEETH ADJUSTING BRACKET AND THE METHOD FOR ORTHODONTICS ADJUSTING THEREOF

(71) Applicant: Yu-Hua Lu, Taipei (TW)

(72) Inventor: Yu-Hua Lu, Taipei (TW)

( * ) Notice: Subject to any disclaimer, the term of this patent is extended or adjusted under 35 U.S.C. 154(b) by 224 days.

(21) Appl. No.: 14/460,641

(22) Filed: Aug. 15, 2014

(65) Prior Publication Data

US 2016/0045287 A1 Feb. 18, 2016

(51) Int. Cl.
*A61C 7/28* (2006.01)

(52) U.S. Cl.
CPC .................... *A61C 7/282* (2013.01)

(58) Field of Classification Search
CPC .................. A61C 7/14; A61C 7/282
See application file for complete search history.

(56) References Cited

U.S. PATENT DOCUMENTS

| 3,218,713 | A | * | 11/1965 | Wallshein | ................ A61C 7/12 433/11 |
| 3,765,091 | A | * | 10/1973 | Northcutt | ................ A61C 7/12 433/9 |
| RE28,962 | E | * | 9/1976 | Wallshein | ............... A61C 7/282 433/16 |

* cited by examiner

*Primary Examiner* — Rex R Holmes
(74) *Attorney, Agent, or Firm* — WPAT, PC; Justin King; Jonathan Chiang

(57) ABSTRACT

This invention discloses an orthodontics adjusting bracket changing the traditional orthodontics logical thinking. The orthodontics adjusting bracket can reduce the chance for removing teeth, decrease the sequelae of removing wisdom teeth, avoid temporomandibular joint-pain-dysfunction syndrome and cheeks depressed, extend lifetime of dental formula, and lower down the social security expenditure. This invention can fundamentally improve dental engagement to avoid the secondary injury of traditional orthodontics treatment and improve the loading of social security expenditure. According to this invention, the difficult mission of correcting wisdom teeth in traditional orthodontics treatment will become easily and smoothly.

11 Claims, 7 Drawing Sheets

WISDOM TEETH ADJUSTING BRACKET AND THE METHOD FOR ORTHODONTICS ADJUSTING THEREOF

BACKGROUND OF THE INVENTION

1. Field of the Invention

The present invention is generally related to an auxiliary device for orthodontics, and more particularly to wisdom teeth adjusting bracket and the method for orthodontics adjusting thereof.

2. Description of the Prior Art

Recently, orthodontics becomes a popular issue. In the past 125 years, wisdom teeth are usually thought as useless and as an unstable reason to the result of orthodontics being able to bring un-convenient and bother the patients and the doctors. In many industrialized countries, including the specialist training and the logical thinking of clinical treatment, it is hard to avoid the consideration for speedy accomplishing orthodontics treatment. Therefore, the considered orthodontics program is usually inclined to perform surgery for removing patient's wisdom teeth. The above-mentioned orthodontics program can easily and speedy correct the teeth arrangement of the patients. But, the above-mentioned "speedy" orthodontics program also brings lots of sequelae. The majorly known sequelae are shown as the following.

1. After removing a patient's wisdom teeth, the bite pivots of the patient will be moved forward, and temporomandibular joint-pain-dysfunction syndrome will be caused therefrom.

2. If removed patient's wisdom teeth, the periodontal damage at the distal side of the patient's secondary molar may not be repaired by specific differentiation, no matter caused by innate or acquired reasons.

3. If the pre-molars and wisdom teeth are removed before adult, there will be some defects formed in the teeth conformation. When the dental formula of the patient grown up, the patient's cheeks will become depressed and the nasolabial folds will come out earlier than usual.

4. Theoretically, wisdom teeth are most young teeth with longest lifetime. If removing wisdom teeth before orthodontics treatment, the lifetime of all teeth will be decreased.

5. The loading of the patient's insurance and the social security will be substantially increased by the therapy cost of the orthodontics sequelae. If the orthodontics sequelae can be efficiently controlled, the expenditure of social security and personal insurance will be decreased.

Besides, for orthodontics operator, to correct tipped teeth is one of the most popular and most difficult clinical works. In the traditional orthodontics treatment, it is hard to place bracket and correcting wire onto the target wisdom teeth. For a wisdom tooth with tipping angle about 30 to 90 degrees, to perform an adjusting program to correct the wisdom tooth during the orthodontics treatment is almost impossible. Therefore, it seems very logically to remove the wisdom teeth through a surgery operation in the traditional orthodontics treatment.

Excluding the mentioned sequelae, removing wisdom teeth by surgery operation will increase the uncomfortableness and infection chance of the patients. Moreover, for some patients unsuited for performing surgery, such as patients with blood coagulation disease or weak immunity, it would be a hard decision to perform the surgery for removing the wisdom teeth during orthodontics treatment.

In view of the above matters, developing a novel wisdom-teeth adjusting bracket and the method for orthodontics adjusting thereof having the advantage of efficiently decreasing the sequelae come with the orthodontics treatment is still an important task for the industry.

SUMMARY OF THE INVENTION

In light of the above background, in order to fulfill the requirements of the industry, the present invention provides a novel wisdom teeth adjusting bracket and the method for orthodontics adjusting thereof having the advantage of easily operating and occupying few space. More preferably, the wisdom teeth adjusting bracket and the method for orthodontics adjusting thereof of this invention can efficiently correct wisdom teeth without any operation for removing the wisdom teeth/tooth, so that the mentioned wisdom teeth adjusting bracket and the method for orthodontics adjusting thereof can be more popular for orthodontics patients with more safety and efficiently.

One objective of the present invention is to provide a wisdom teeth adjusting bracket and the method for orthodontics adjusting thereof to perfectly correct wisdom teeth through physical stress during orthodontics treatment. Preferably, according to this specification, the orthodontics treatment can be performed without surgery operation and approach the purpose of maintaining all teeth without removing wisdom teeth.

Another objective of the present invention is to provide a wisdom teeth adjusting bracket and the method for orthodontics adjusting thereof to correct wisdom teeth with orthodontics correcting tubes of the wisdom teeth adjusting bracket with different angles. Preferably, according to this specification, the wisdom teeth do not need to be removed by surgery operation, and the orthodontics treatment can be modulated by each of the tipping angle of the target wisdom teeth.

Accordingly, the present invention discloses a wisdom teeth adjusting bracket and the method for orthodontics adjusting thereof. In one preferred example of this specification, the mentioned wisdom teeth adjusting bracket comprises a tooth surface attachment base plate, and at least two orthodontics correcting tubes positioned at the same side of the tooth surface attachment base plate. There is an angle between the orthodontics correcting tubes.

In another preferred example of this invention, wisdom teeth adjusting bracket comprises a tooth surface attachment base plate, and a bracket body positioned on the tooth surface attachment base plate. The bracket body comprises at least two orthodontics correcting tubes. Each of the orthodontics correcting tubes is passed through the bracket body. There is an angle between every two of the orthodontics correcting tubes.

In another preferred example of this invention, the mentioned method for orthodontics adjusting comprises providing a wisdom teeth adjusting bracket, attaching the wisdom teeth adjusting bracket onto the surface of a target wisdom tooth, passing a correcting wire through a first orthodontics correcting tube of the wisdom teeth adjusting bracket, and pulling out the correcting wire and passing the correcting wire through a second orthodontics correcting tube of the wisdom teeth adjusting bracket.

BRIEF DESCRIPTION OF THE DRAWINGS

The present disclosure can be described by the embodiments given below. It is understood, however, that the FIG. 1 shows a wisdom teeth adjusting bracket of this invention;

FIG. 3 shows a flowchart of the method for

DESCRIPTION OF THE PREFERRED EMBODIMENTS

What probed into the invention is a wisdom teeth adjusting bracket and the method for orthodontics adjusting thereof. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
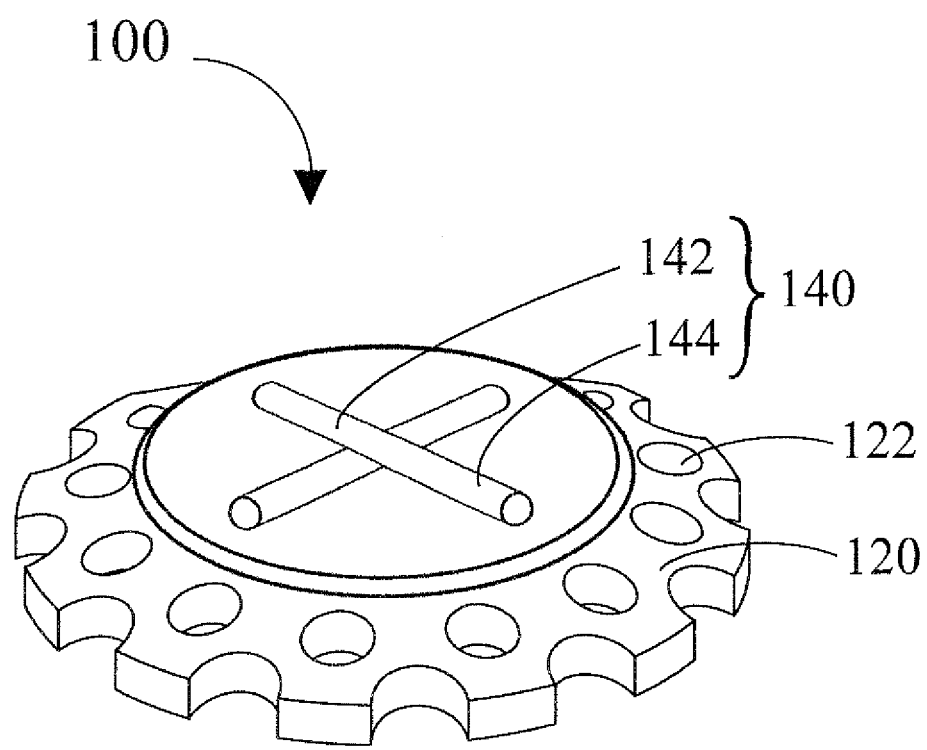

One preferred embodiment according to this specification discloses a wisdom teeth adjusting bracket. FIG. 1 shows a wisdom teeth adjusting bracket of this embodiment. Referred to FIG. 1, the mentioned wisdom teeth adjusting bracket 100 comprises a tooth surface attachment base plate 120, and at least two orthodontics correcting tubes 140. The orthodontics correcting tubes are positioned at the same side of the tooth surface attachment base plate 120. In one preferred example of this embodiment, the orthodontics correcting tubes 140 are fixed onto the tooth surface attachment base plate 120 through any well-known method, such as welding. In another preferred example of this embodiment, the orthodontics correcting tubes 140 and the tooth surface attachment base plate 120 are integrally formed.

According to this embodiment, the tooth surface attachment base plate 120 comprises a plurality of openings 122. In one preferred example, the openings 122 can be irregularly distributed over the tooth surface attachment base plate 120. In another example, the openings 122 can be distributed around the edge of the tooth surface attachment base plate 120. Each of the openings 122 is passed through the tooth surface attachment base plate 120. When the tooth surface attachment base plate 120 is attached onto the surface of the target wisdom tooth by gluing, part of the glue will spill over the openings 122 so that the tooth surface attachment base plate 120 will be tightly attached onto the surface of the target wisdom tooth.

According to this embodiment, there is an angle between every two of the orthodontics correcting tubes 140. The mentioned angle is about 30 to 75 degrees. In one preferred example of this embodiment, the mentioned angle is about 45 degrees. In another preferred example, the mentioned angle is about 60 degrees.

In one preferred example of this embodiment, the method for orthodontics adjusting through employing the wisdom teeth adjusting bracket 100 can be performed as the following. Firstly, the wisdom teeth adjusting bracket 100 is attached onto the surface of the target wisdom tooth at a proper position. A correcting wire is passed across a first orthodontics correcting tube 142 of the orthodontics correcting tubes 140 of the wisdom teeth adjusting bracket 100, and the both ends of the correcting wire are fixed. Through the physical stress of the correcting wire, the target wisdom tooth will be corrected to a first position. Then, the corrected wire is pulled out and passed through a second orthodontics correcting tube 144 of the orthodontics correcting tubes 140. Through the physical stress of the correcting wire, the target wisdom tooth will be corrected from the first position to a second position. In one preferred example, if the second orthodontics correcting tube still cannot completely correct the target wisdom tooth, the above steps can be repeat as passing the correcting wire through the first orthodontics correcting tube or a third orthodontics correcting tube (not shown in the figure) for further correcting the target wisdom tooth.

Figure 2A:
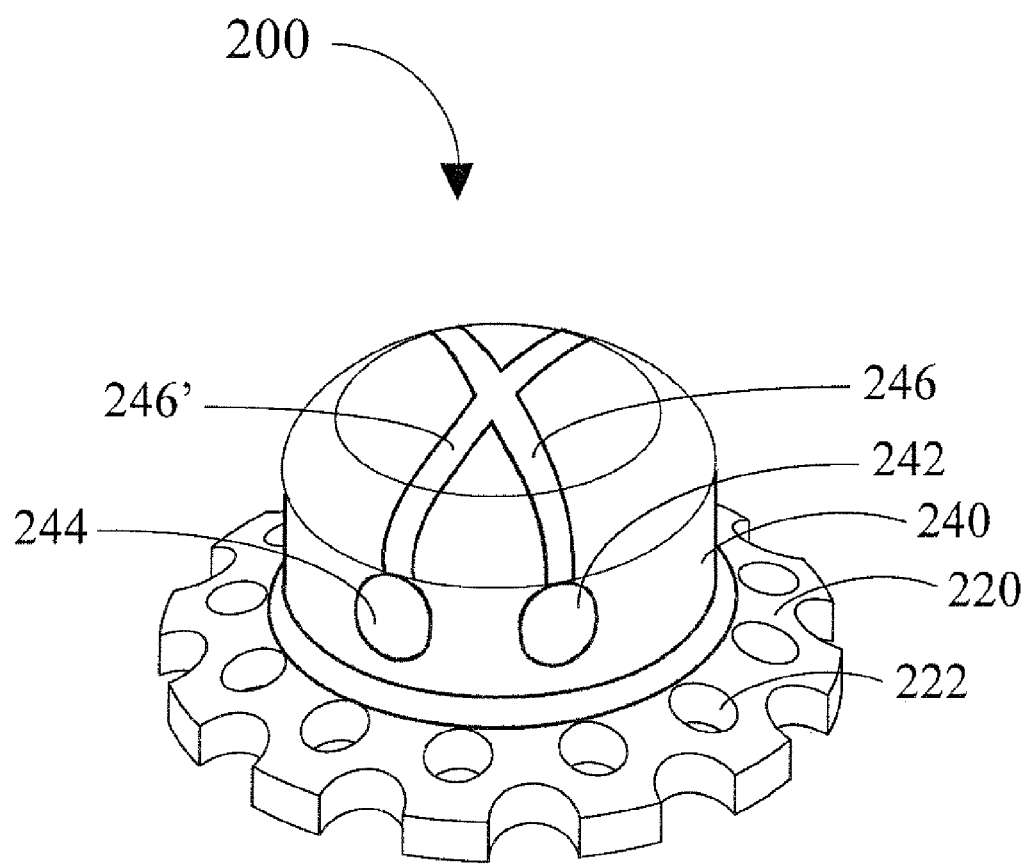
FIG. 2A and FIG. 2B shows another wisdom teeth adjusting bracket of this invention.
Figure 2B:
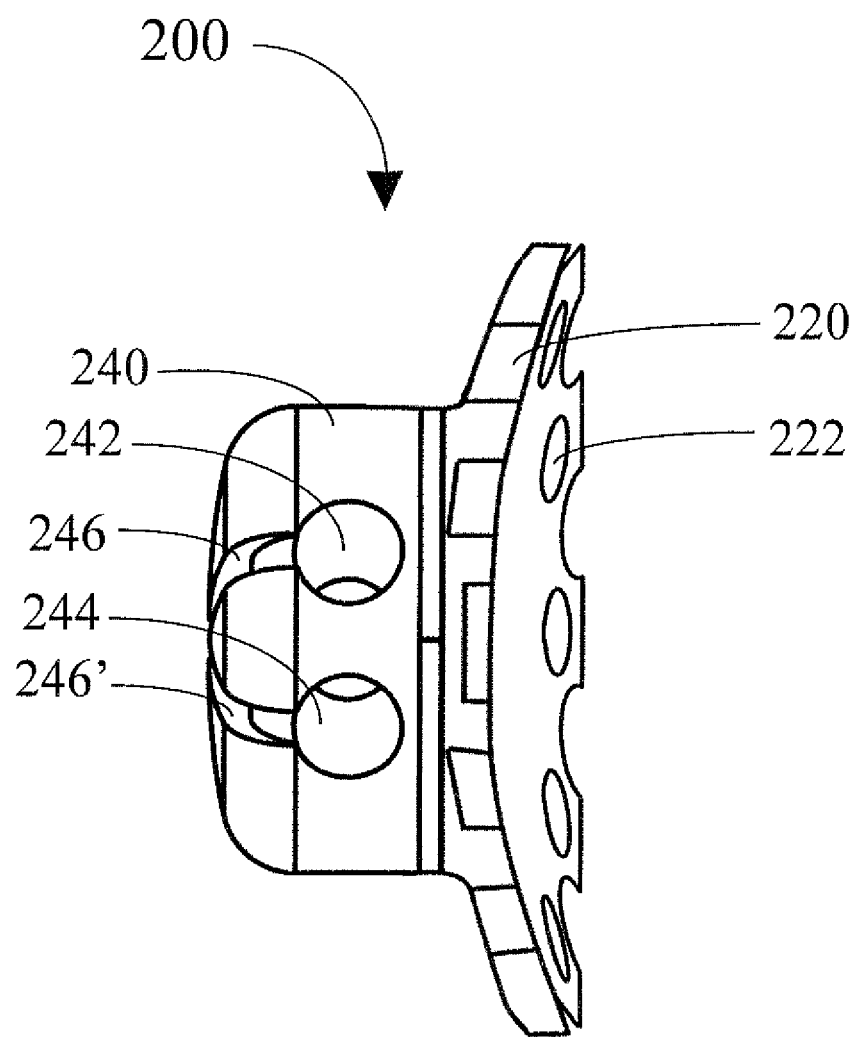

Another preferred embodiment of this specification discloses a wisdom teeth adjusting bracket. FIG. 2A and FIG. 2B show a wisdom teeth adjusting bracket of this embodiment. Referred to FIG. 2A and FIG. 2B, the wisdom teeth adjusting bracket 200 comprises a tooth surface attachment base plate 220, and a bracket body 240. The bracket body 240 is positioned on the tooth surface attachment base plate 220. According to this embodiment, the bracket body 240 is extended from the tooth surface attachment base plate 220. In one preferred example, the bracket body 240 is combined with the tooth surface attachment base plate 220 through any technology known by the one skilled in the art, such as welding. In another example, the bracket body 240 and the tooth surface attachment base plate 220 are integrally formed.

The tooth surface attachment base plate 220 comprises a plurality of openings 222. In one preferred example, the openings 222 can be irregularly distributed over the tooth surface attachment base plate 220. In another example, the openings 222 can be distributed around the edge of the tooth surface attachment base plate 220. The wisdom teeth adjusting bracket 200 can be attached onto a surface of a target wisdom tooth by gluing. When attaching the wisdom teeth adjusting bracket 200 onto a surface of a target wisdom tooth by gluing, some glue will spill over the openings 222 from the surface of the target wisdom tooth, so that the wisdom teeth adjusting bracket 200 will be tightly attached onto the surface of the target wisdom tooth.

The bracket body 240 comprises at least two orthodontics correcting tubes, shown as 242 and 244 in FIG. 2A and FIG. 2B. The orthodontics correcting tubes are individually passed through the bracket body 240. There is an angle between the orthodontics correcting tubes. The range of the mentioned angle is about 30 to 75 degrees. In one preferred example of this embodiment, the mentioned angle is about 45 degrees. In another preferred example, the mentioned angle is about 60 degrees.

In one preferred example of this embodiment, the bracket body 240 further comprises at least two trench 246 and 246'. The trenches 246 and 246' are positioned on the bracket body 240, and the direction of each trench is independently corresponding to one of the orthodontics correcting tubes. Because the size of the wisdom teeth adjusting bracket 200 is very tiny, the mentioned trenches are helpful on identifying the location and direction of the orthodontics correcting tubes during fastening the wisdom teeth adjusting bracket 200 or passing a correcting wire through one of the orthodontics correcting tubes.

Figure 3:
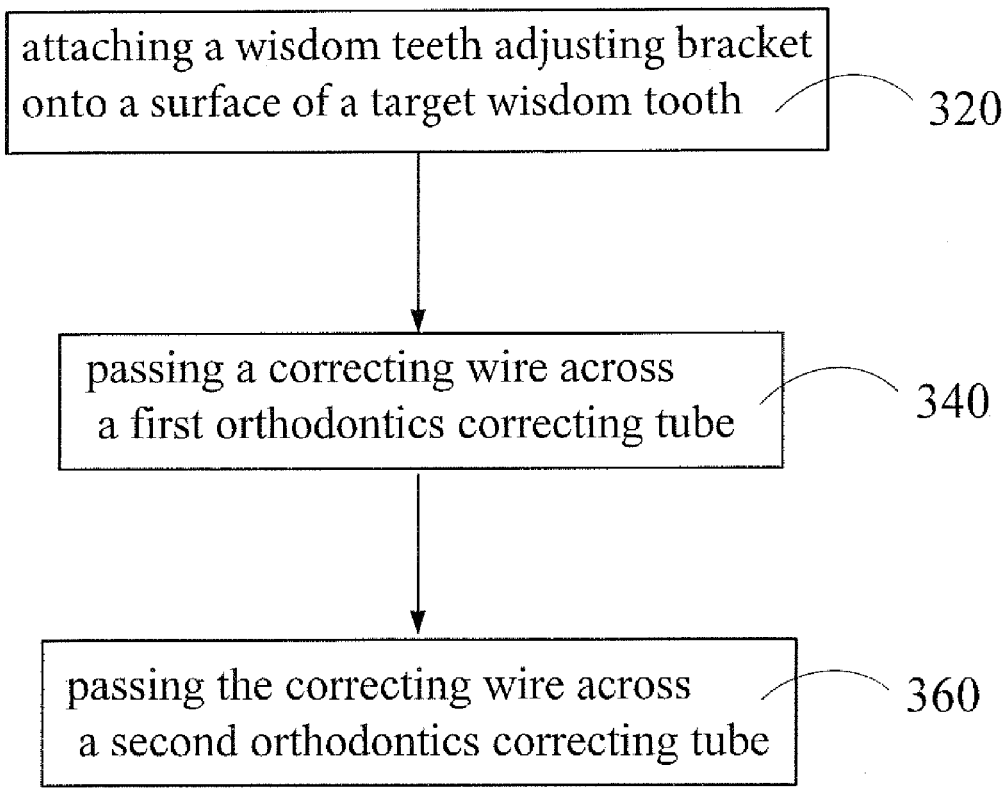

Still another preferred embodiment of this specification discloses a method for orthodontics adjusting with wisdom teeth adjusting bracket. FIG. 3 shows a flowchart of the mentioned method of this embodiment. Referred to FIG. 3, the method for orthodontics adjusting with wisdom teeth adjusting bracket comprises the step 320 of attaching a wisdom teeth adjusting bracket onto a surface of a target wisdom tooth, the step 340 of passing a correcting wire through a first orthodontics correcting tube of the wisdom teeth adjusting bracket, and the step 360 of passing the correcting wire through a second orthodontics correcting tube of the wisdom teeth adjusting bracket.

In the step 320, the wisdom teeth adjusting bracket can be attached onto the outside surface of the target wisdom tooth by gluing. In one preferred example of this embodiment, the mentioned wisdom teeth adjusting bracket is as the wisdom teeth adjusting bracket shown in FIG. 1. In another preferred example, the mentioned wisdom teeth adjusting bracket is as the wisdom teeth adjusting bracket shown in FIGS. 2A and 2B. When attaching the wisdom teeth adjusting bracket onto the surface of the target wisdom tooth, the position of the wisdom teeth adjusting bracket and the angle between the first orthodontics correcting tube of the wisdom teeth adjusting bracket and the gums can be decided upon how crooked the target wisdom tooth is.

Figure 4A:
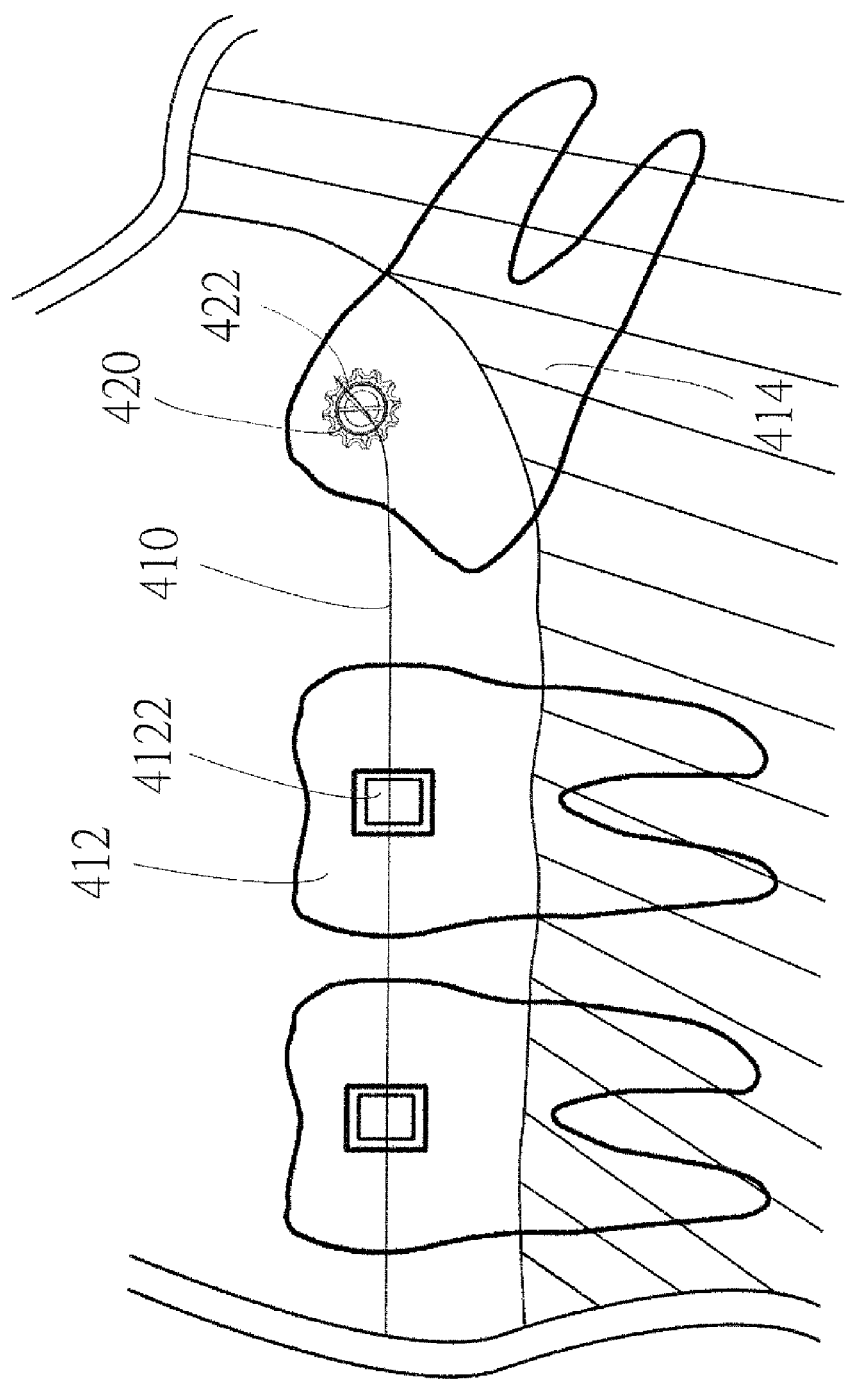
FIG. 4A to FIG. 4C shows an orthodontics treatment of this invention.
Figure 4B:
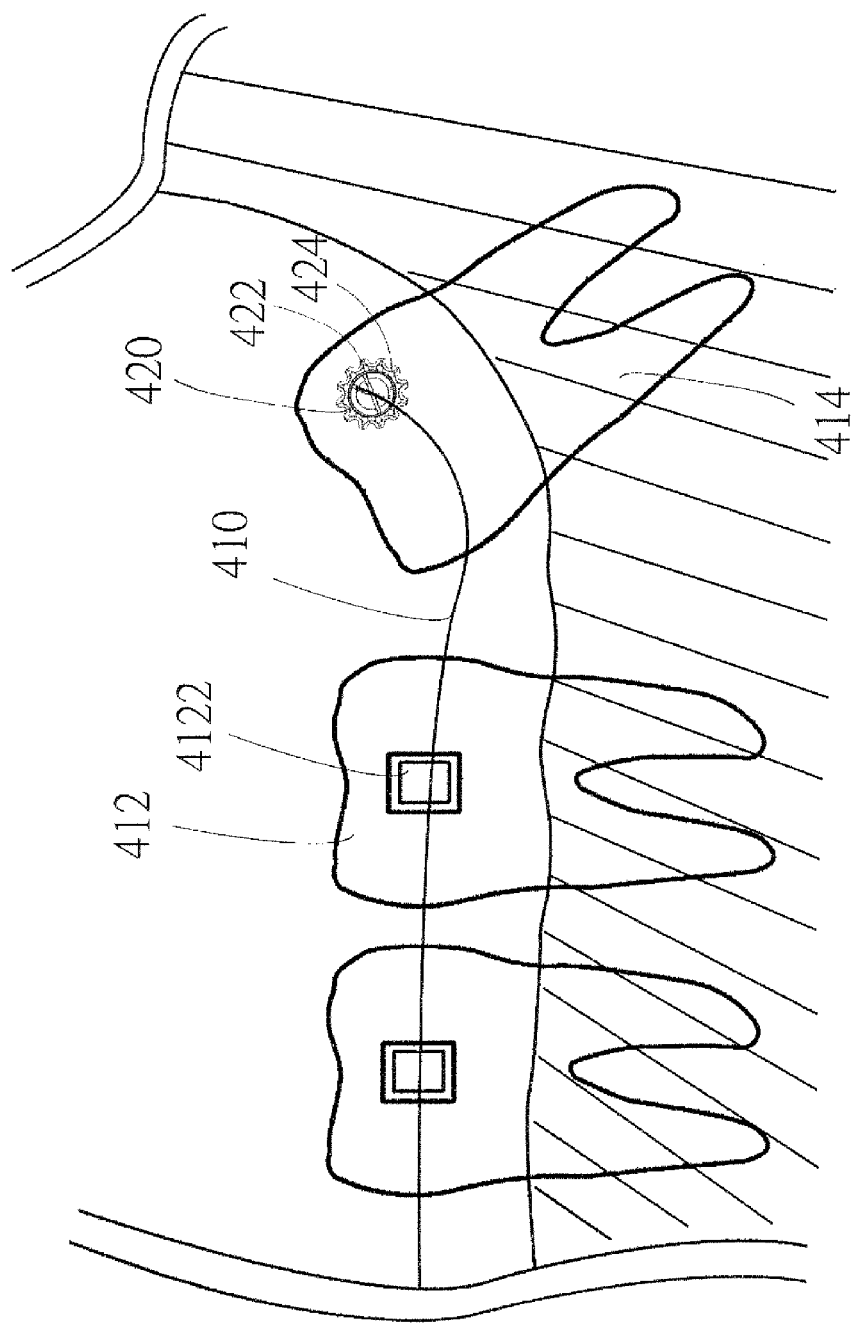
Figure 4C:
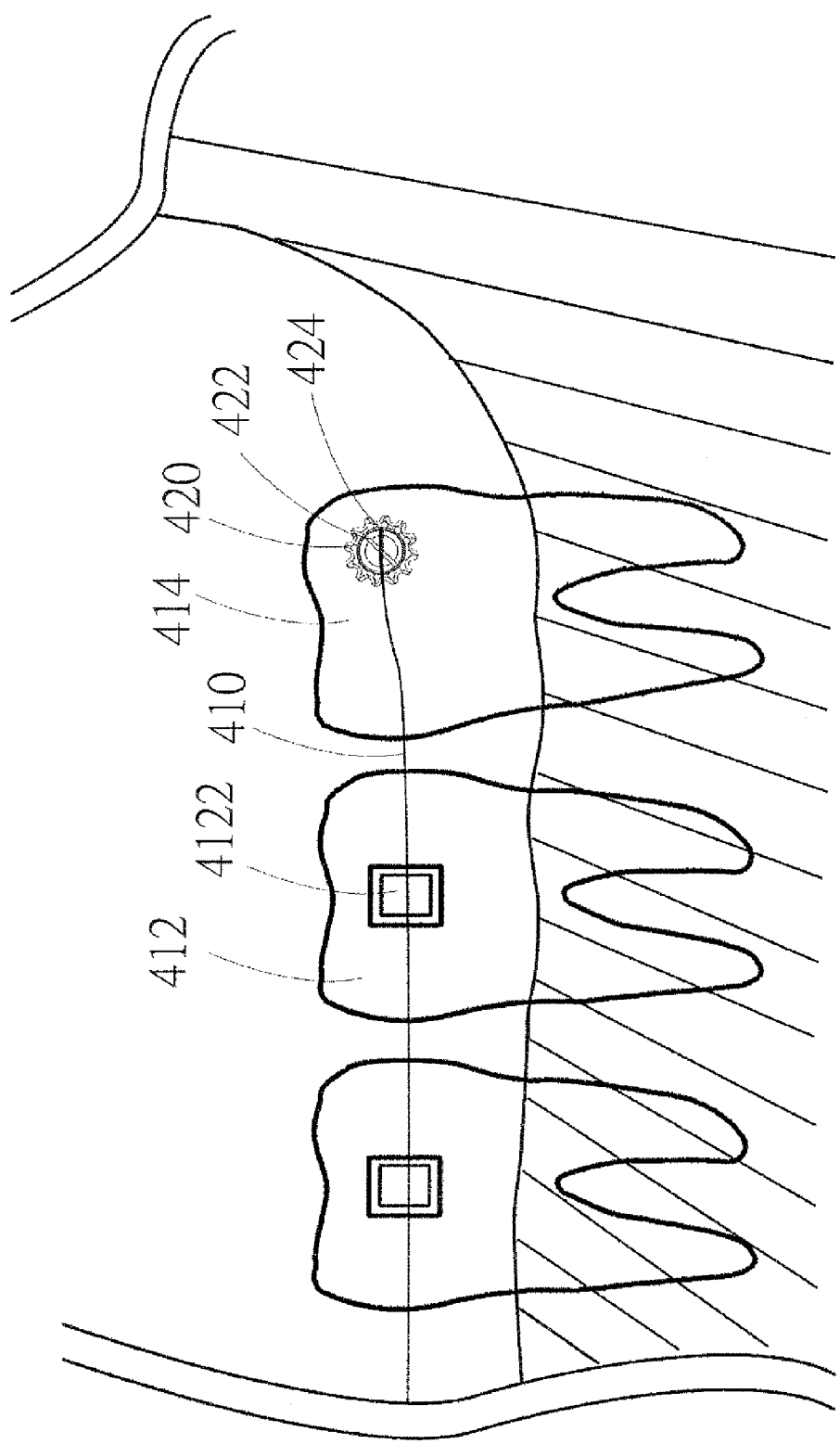

After attaching the wisdom teeth adjusting bracket onto the surface of the target wisdom tooth, a correcting wire is passed through a first orthodontics correcting tube of the wisdom teeth adjusting bracket, shown as the step 340. FIG. 4A to FIG. 4C illustrates an orthodontics treatment process with the wisdom teeth adjusting bracket of this embodiment. Referred to FIG. 4A, a correcting wire 410 is passed through a bracket 4122 on a neighboring tooth 412, and passed the first orthodontics correcting tube 422 of the wisdom teeth adjusting bracket 420 on the target wisdom tooth 414.

According to the physical stress of the correcting wire 410, the target wisdom tooth 414 will be corrected to a first position. Subsequently, if further orthodontics correction is necessary for the target wisdom, the correcting wire 410 will be pulled out from the first orthodontics correcting tube 422 and passed through the second orthodontics correcting tube 424 of the wisdom teeth adjusting bracket 420, as shown in the step 360 in FIG. 3 and as shown in FIG. 4B. So that the correcting wire 410 can provide enough physical stress for further correcting the target wisdom tooth 414.

By the physical stress of the correcting wire 410 passed through the second orthodontics correcting tube 424 after the step 360, the target wisdom tooth 414 will be corrected to a wanted position and angle. In one preferred example of this embodiment, for some wisdom teeth with larger inclined angle or some wisdom teeth required smooth orthodontics correcting process, the target wisdom tooth may not be completely corrected after the step 360. In order to completely orthodontics correcting the target wisdom tooth, the step 340 or the steps 340 and 360 in FIG. 3 can be repeated, as shown in FIG. 4C.

In summary, we have reported a wisdom teeth adjusting bracket and the method for orthodontics adjusting thereof. The mentioned wisdom teeth adjusting bracket comprises a tooth surface attachment base plate, and at least two orthodontics correcting tubes positioned at the same side of the tooth surface attachment base plate. There is an angle between the orthodontics correcting tubes. During orthodontics treatment, by sequentially passing through different orthodontics correcting tubes of the wisdom teeth adjusting bracket, the correcting wire can provide enough stress for correcting the target wisdom tooth to wanted corrective position and angle. According to this specification, instead of removed by surgery operation in traditional orthodontics treatment, a wisdom tooth can be easily and efficiently corrected by physical stress from a correcting wire. So that the orthodontics treatment according to this specification can approach the purpose of maintaining all teeth without removing wisdom teeth. Preferably, without performing surgery to remove teeth, the orthodontics treatment according to this specification can efficiently decrease the uncomfortable-ness and infection of the patients, and the technology disclosed in this specification also can efficiently decrease the sequela in the traditional orthodontics treatment with surgery for removing wisdom teeth. More preferably, for those patients unsuited for performing surgery, such as patients with blood coagulation disease or weak immunity, the technology of this specification still can provide them a safe orthodontics treatment.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A wisdom teeth adjusting bracket, comprising:
 a tooth surface attachment base plate, wherein said tooth surface attachment base plate comprises a plurality of openings, wherein said openings are distributed over said tooth surface attachment base plate, and each opening passes through said tooth surface attachment base plate; and
 at least two orthodontics correcting tubes positioned at the same side of said tooth surface attachment base plate, wherein said orthodontic correcting tubes overlap or intersect at an angle between 30 degrees to 75 degrees;
 wherein, said correcting tubes are cylindrical in shape to allow a correcting wire to pass through said correcting tubes.

2. The wisdom teeth adjusting bracket according to claim 1, wherein said angle is 45 degrees.

3. The wisdom teeth adjusting bracket according to claim 1, wherein said angle is 60 degrees.

4. The wisdom teeth adjusting bracket according to claim 1, further comprising a bracket body, wherein said orthodontics correcting tubes are individually pass through said bracket body.

5. The wisdom teeth adjusting bracket according to claim 4, wherein said bracket body and said tooth surface attachment base plate are integrally formed.

6. The wisdom teeth adjusting bracket according to claim 4, wherein said bracket body comprises at least two trenches, wherein the direction of each trench is corresponding to one of said orthodontics correcting tubes.

7. A wisdom teeth adjusting bracket, comprising:
 a tooth surface attachment base plate, wherein said tooth surface attachment base plate comprises a plurality of openings, wherein said openings are distributed over said tooth surface attachment base plate, and each opening passes through said tooth surface attachment base plate; and
 a bracket body positioned on said tooth surface attachment base plate, wherein said bracket body comprises at least two orthodontics correcting tubes, wherein said orthodontics correcting tubes individually pass through said bracket body, wherein said orthodontic correcting tubes intersect or overlap at an angle between 30 degrees to 75 degrees.

8. The wisdom teeth adjusting bracket according to claim 7, wherein said angle is 45 degrees.

9. The wisdom teeth adjusting bracket according to claim 7, wherein said angle is 60 degrees.

10. The wisdom teeth adjusting bracket according to claim 7, wherein said bracket body and said tooth surface attachment base plate are integrally formed.

11. The wisdom teeth adjusting bracket according to claim 7, wherein said bracket body comprises at least two trenches, wherein the direction of each trench is corresponding to one of said orthodontics correcting tubes.

* * * * *